US005304807A

United States Patent [19]
Lin

[11] Patent Number: 5,304,807
[45] Date of Patent: Apr. 19, 1994

[54] METHOD FOR DETERMINING THE DEGRADATION OF FUEL OIL BY UV ABSORPTION

[75] Inventor: Fan-Nan Lin, Bartlesville, Okla.

[73] Assignee: Phillips Petroleum Company, Bartlesville, Okla.

[21] Appl. No.: 981,623

[22] Filed: Nov. 25, 1992

[51] Int. Cl.$^5$ ............... G01N 33/22; G01N 21/17
[52] U.S. Cl. ................ 250/373; 250/301; 250/372
[58] Field of Search .......... 250/373, 343, 372, 301; 356/70; 44/903

[56] References Cited

U.S. PATENT DOCUMENTS

| | | | |
|---|---|---|---|
| 3,578,865 | 5/1971 | Traver | 356/70 |
| 4,556,326 | 12/1985 | Kitchen, III et al. | 374/45 |
| 4,628,204 | 12/1986 | Maes | 356/70 X |
| 4,783,416 | 11/1988 | Patel | 250/373 X |

FOREIGN PATENT DOCUMENTS

| | | | |
|---|---|---|---|
| 58-100739 | 6/1983 | Japan | 356/70 |
| 63-63968 | 3/1988 | Japan | 356/70 |
| 2-236440 | 9/1990 | Japan | 356/70 |

OTHER PUBLICATIONS

B. D. Batts and A. Zuhdan Fathoni, "A Literature Review on Fuel Stability Studies with Particular Emphasis on Diesel Oil"; *Energy and Fuels*, vol. 5, No. 1, pp. 2–21, 1991.

Petroleum Refining & Petrochemicals/Literature, Petroleum Processing: Hydrogenation Jun. 15, 1992, p. 2.

*Primary Examiner*—Constantine Hannaher
*Assistant Examiner*—Edward J. Glick
*Attorney, Agent, or Firm*—Ryan N. Cross

[57] ABSTRACT

A method for determining the suitability of a distillate fuel for use after storage by measuring the absorption of ultraviolet light by the fuel.

14 Claims, 2 Drawing Sheets

METHOD FOR DETERMINING THE DEGRADATION OF FUEL OIL BY UV ABSORPTION

BACKGROUND OF THE INVENTION

This invention relates to a method for determining the degradation that will occur in distillate fuel oils over a period of time.

During hydrocarbon processing, transportation and storage, the hydrocarbons deteriorate, particularly when subjected to elevated temperatures. The deterioration usually results in the formation of sediment, sludge, or gum, and can manifest itself physically by color deterioration. Sediment, sludge, or gum formation can cause clotting of the equipment or fouling of processing equipment, such as heat exchangers, compressors, furnaces, reactors and distillation systems, as examples. The fouling can be caused by the gradual accumulation of high molecular weight polymeric material on the inside surfaces of the equipment. As fouling continues, the efficiency of the operation associated with the hydrocarbon processing equipment, such as heat exchangers, compressors, furnaces, reactors and distillation systems decreases. The distillate streams, which can result in significant fouling, include the straight run distillates (kerosene, diesel, jet) naphthas, catalytic cracker feedstocks (gas oils), light and heavy cycle oils, coker napthas, resids and petrochemical plant feedstocks.

In the past, methods for determining the deterioration of fuel oil over a period of time, such as during storage, transportation or processing of the fuel oil, have relied on sampling the fuel after the period of time has past. Thus, they have been insufficient for predicting the deterioration of the fuel prior to such deterioration occurring. It is desirable to have a test method that is capable of determining not only the present state of a fuel oil but, also, is capable of predicting the state of a fuel oil after a period of time and predicting the rate of degradation of the fuel oil.

SUMMARY OF THE INVENTION

It is therefore, an objective of the present invention to provide a method for determining the present state of a fuel oil.

It is a further object of the present invention to provide a method of predicting the rate of degradation of a fuel oil.

It is still another objective of the present invention to provide a method for predicting the amount of degradation that will occur in a fuel oil after a period of time.

The above objects are realized in a method which comprises: measuring the absorption of ultraviolet light by a sample of a distillate fuel oil between 360 and 385 nm to obtain a first measurement; and determining from the measurement the suitability of the distillate fuel oil for use after storage.

DESCRIPTION OF THE PREFERRED EMBODIMENTS

Figure 1:
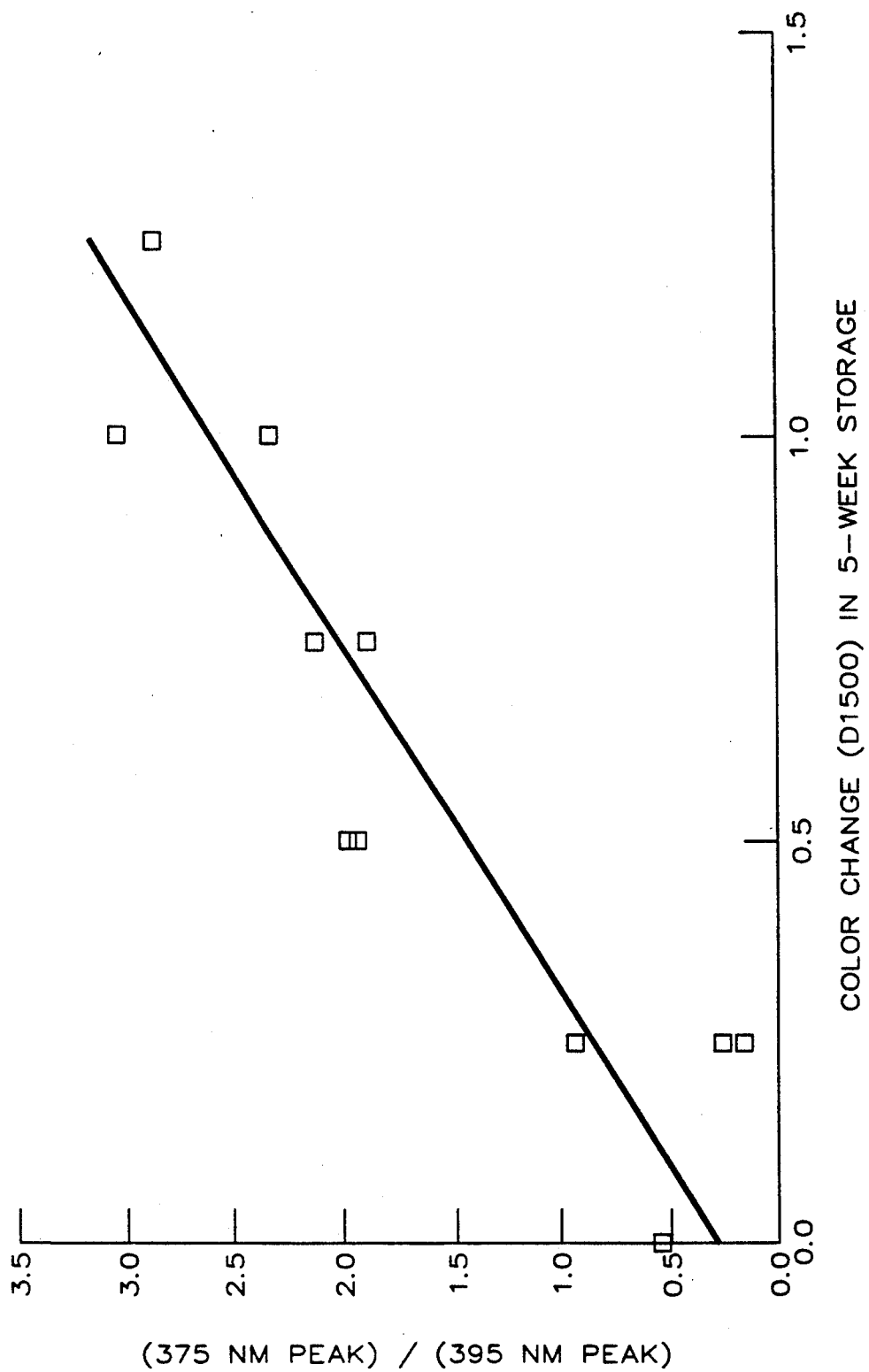
FIG. 1 is a graphical representation of the correlation between the degradation of different fuel oils and the 375 nm ultraviolet absorption peak of the fuel oils.

The present invention pertains to using the absorption spectra of a sample of a distillate fuel oil to determine the degradation of the distillate fuel oil.

Degradation of the fuel oil, as used herein, refers to color degradation, particulate and sediment formation and/or gum generation.

Generally, the distillate fuel oils that the process can be used on include the straight run distillates (kerosene, diesel, jet) naphthas, catalytic cracker feedstocks (gas oils), light and heavy cycle oils, coker naphthas, resids, petrochemical plant feedstocks and hydrotreated distillate fuel oils thereof. Preferred distillate fuel oils are straight run distillates, light and heavy cycle oils, hydrotreated straight run distillates, and hydrotreated light and heavy cycle oils.

According to the present invention, an ultraviolet (UV) absorption spectrum for a distillate fuel oil is taken in order to measure the height above the baseline of the 375 nm peak, that is the ultraviolet peak in a range of from about 360 to about 385 nm, preferably from 370 nm to 380 nm, more preferably at about 375 nm, and most preferably at 375 nm. This peak height can be correlated directly with the instability of the fuel.

In a preferred embodiment, the distillate fuel oil is first filtered and then, if desired, a solvent can be used to dilute the distillate fuel oil. Pre-filtering serves to eliminate or minimize high molecular weight gums which are characterized by light absorbance at wavelengths higher than 450 nm. The major purpose of fuel dilution is to obtain a good UV-spectrum. Generally, straight run distillates or kerosenes free from light cycle oils are light enough in color that no solvent dilution is required. However, other fuel oils, such as light cycle oils, can require a solvent to obtain a suitable UV-spectrum because of their dark color. The diluent solvent should be one that is completely miscible with the fuel, does not produce any phase separation and does not hinder the taking of the UV absorption spectra. Examples of suitable solvents are methanol, xylene, nitromethylene, kerosenes, and gasolines. Presently, methanol and xylene are preferred.

Next, the height of the 375 nm peak is determined. Additionally, the height of the 395 nm peak, that is the UV peak in the range from about 390 to about 430 nm, preferably about 395 nm, and most preferably at 395 nm, is determined.

Any conventional method can be used to calculate the peak height. A preferred method is a 3-point method. For example, for the 375 nm peak, a UV spectrum is taken and, in addition to a value for 375 nm absorbance, values for two additional wave lengths outside the 375 nm peak range are measured to determine the baseline, for example, a 368 nm absorbance and a 389 nm absorbance can be obtained. In this example the 375 nm peak height would be calculated as follows:

$$(375 \text{ nm peak height}) = (375 \text{ absorbance}) - (1/3) \cdot [2 \cdot (368 \text{ nm absorbance}) + (389 \text{ nm absorbance})]$$

Upon obtaining the 375 nm peak measurement and 395 nm peak measurement, the two measurements are correlated to determine the instability of the fuel. The ratio of the 375 nm peak measurement to the 395 nm peak measurement will be proportional to the color change and, thus, to the rate of formation of gums and sediments, because the greater the color change the greater the amount of gums formed and, eventually, the greater the amount of sediment formed.

While not wishing to be bound by theory, it is believed that the 375 nm absorption indicates the presence of a precursor, believed to be phenalenone, to the formation of gums and sediments and the 395 nm absorption indicates the presence of the initial gums formed in the fuel oil as it degrades. The greater the ratio of the 375 nm absorption to 395 nm absorption the faster the formation of more gum and, ultimately, the more sediment produced.

In order to more clearly illustrate this invention, the data set forth below was developed. The following examples are included as being illustrations of the invention and should not be construed as limiting the scope thereof.

EXAMPLES

EXAMPLE I

Samples of various distillate fuels were obtained. These samples were either light cycle oils (LCO) or straight run distillates (SRD) and were obtained from three different refineries. The samples were filtered using a 0.45 micrometer membrane filter. 0.02 cm$^3$ of each of the LCO samples were diluted with 9.98 cm$^3$ of a solvent to give 10.00 cm$^3$ diluted LCO samples. A UV spectrum of each of the 10.0 cm$^3$ diluted LCO samples and of 1.0 cc of each undiluted SRD sample was taken. The UV spectra were taken using a Milton-Roy spectrophotometer, Model Spectronic 1201. The UV-absorbance spectra were obtained in a wavelength-scan mode between 300 nm and 900 nm (more typically, between 350 nm and 750 nm to avoid the routine switching of light-source and light detector in the 300 nm to 900 nm operation). The value of the precursor peak at 375 nm was calculated from the UV-spectrum by using the previously mentioned 3-point method. The measurement of 375 nm and 395 nm peaks are recorded in Table I.

The color of the remaining fuel samples was measured according to ASTM-D 1500-87, except that when fuel color was intermediate between the color of two standard glasses. The lighter glass designation was recorded followed by a "+". The results of these measurements are recorded as "initial color" in Table I.

The fuel was then put in a partially capped glass jar, stored and aged at ambient conditions of room temperature and air pressure for 5 weeks and the final color of the aged fuel was measured and recorded in Table I as "final color". The increase of ASTM-D 1500-87 color from the initial value was defined as color instability and is recorded in Table I as "color change" with the "plus" values of the Initial color and final color values calculated as an additional 0.25 to the color glass value.

TABLE I

| Sample No. | Type | 375 nm Peak | 395 nm Peak | 375 nm/ 395 nm | Initial Color | Final Color | Color Change |
|---|---|---|---|---|---|---|---|
| 1 | LCO | 0.569 | 0.269 | 2.12 | 4.0 | 4.5+ | 0.75 |
| 2 | LCO | 0.595 | 0.196 | 3.04 | 3.0 | 4.0 | 1.0 |
| 3 | LCO | 0.320 | 0.165 | 1.94 | 2.0 | 2.5+ | 0.75 |
| 4 | LCO | 0.636 | 0.336 | 1.89 | 5.0 | 5.5+ | 0.75 |
| 5 | LCO | 0.691 | 0.240 | 2.88 | 2.5 | 3.5+ | 1.25 |
| 6 | LCO | 0.331 | 0.351 | 0.94 | 6.5 | 6.5+ | 0.25 |
| 7 | LCO | 0.303 | 0.326 | 0.93 | 6.5 | 6.5+ | 0.25 |
| 8 | LCO | 0.407 | 0.206 | 1.98 | 3.0 | 3.5 | 0.5 |
| 9 | LCO | 0.465 | 0.200 | 2.33 | 2.0 | 3.0 | 1.0 |
| 10 | SRD | 0.006 | 0.028 | 0.21 | 0.5 | 0.5+ | 0.25 |
| 11 | SRD | 0.003 | 0.025 | 0.12 | 0.5 | 0.5+ | 0.25 |
| 12 | SRD | 0.0003 | 0.0005 | 0.54 | 0.5 | 0.5 | 0.0 |

The color change was then correlated with the ratio of the 375 nm peak to 395 nm peak absorbance and the resulting least-squared-fitting was:

(Color change in 5 weeks storage) =

$$[(375 \text{ nm peak}/395 \text{ nm peak}) - 0.271]/2.328.$$

The data and the derived correlation are graphically illustrated in FIG. 1. From the above information, an equation for the color change rate can be derived:

(Color change rate) =

$$[(375 \text{ nm peak}/395 \text{ nm peak}) - 0.271]/2.328/5$$

From the above example it can be seen that the amount of degradation that will occur in a fuel oil over a period of time can be determined by measuring the absorption of ultraviolet light passed through a sample of the fuel oil at about 375 nm; therefore, the suitability of the fuel oil for use after storage can be determined based on the amount of degradation which will occur.

EXAMPLE II

Eleven samples of a LCO were obtained. Ten of the samples were hydrotreated to remove sulfur. The hydrotreating was carried out in a fixed bed reactor (¾ inch (1.9 cm) diameter catalyst laboratory testing units) using a cobalt and molybdenum loaded KF-742 catalyst. The hydrotreating was carried out at 4482 KPa, 2 LHSV, 56.6 m$^3$/160 L H$_2$ and at the temperatures indicated in Table II. The reproducibility of the hydrotreating was enhanced by plugging the top, bottom, and interior furnace zones to reduce thermal gradients caused by air drafts, mixing 1/20 inch (0.13 cm) with 20/40 mesh alundum diluent in five equal lots and packing each log separately in the reactor without a physical separator, such as a screen, so as to reduce catalyst/diluent segregation and improve wetting efficiency. The weight percent (wt-%) sulfur in the untreated sample and the ten hydrotreated samples are shown in Table II.

Next the 375 nm peak and the 395 nm peak of each sample was measured and based on these measurements the color change for each sample after 350 days was predicted using the color change rate formula given above. The measurements and predicted color change are recorded in Table II.

Additionally, the initial color of the fuel samples were determined as in Example I. Then the samples were aged for 350 days followed by a determination of the final color and the color change as in Example I. The measurements of the initial and final color as well as the color change are recorded in Table II for each sample.

TABLE II

| Sample No. | Temp. (°F.) | Sulfur Wt-% | 375 nm Peak | 395 nm Peak | Color Change Predicted | Initial Color | Final Color | Color Change |
| --- | --- | --- | --- | --- | --- | --- | --- | --- |
| 11 | — | 0.353 | 0.471 | 0.302 | — | 5.0+ | 8.0+ | SED* |
| 12 | 350 | 0.322 | 0.046 | 0.049 | 3.05 | 3.0 | 5.5 | 2.5 |
| 13 | 450 | 0.211 | 0.018 | 0.042 | 0.91 | 2.0 | 3.5 | 1.5 |
| 14 | 550 | 0.096 | 0.026 | 0.060 | 0.93 | 1.5+ | 2.5 | 0.75 |
| 15 | 650 | 0.016 | 0.023 | 0.098 | 0.10 | 2.5 | 2.5 | 0.0 |
| 16 | 650 | 0.012 | 0.024 | 0.087 | 0.28 | 2.5 | 2.5 | 0.0 |
| 17 | 700 | 0.089 | 0.054 | 0.160 | 0.53 | 3.0 | 4.0 | 1.0 |
| 18 | 750 | 0.014 | 0.130 | 0.186 | 2.05 | 4.0+ | 6.0 | 1.75 |
| 19 | 750 | 0.016 | 0.138 | 0.163 | 2.66 | 2.5+ | 5.5 | 2.75 |
| 20 | 750 | 0.016 | 0.134 | 0.119 | 3.83 | 1.5+ | 6.0 | 4.25 |
| 21 | 750 | 0.017 | 0.116 | 0.096 | 4.18 | 1.5+ | 6.0 | 4.25 |

*Sedimentation occurred in this sample resulting in a color change of 3.0.

In Table II, no value for the predicted color change is recorded for the nonhydrotreated LCO sample because the long storage time resulted in sedimentation formation which lessened the final color of the LCO sample.

Figure 2:
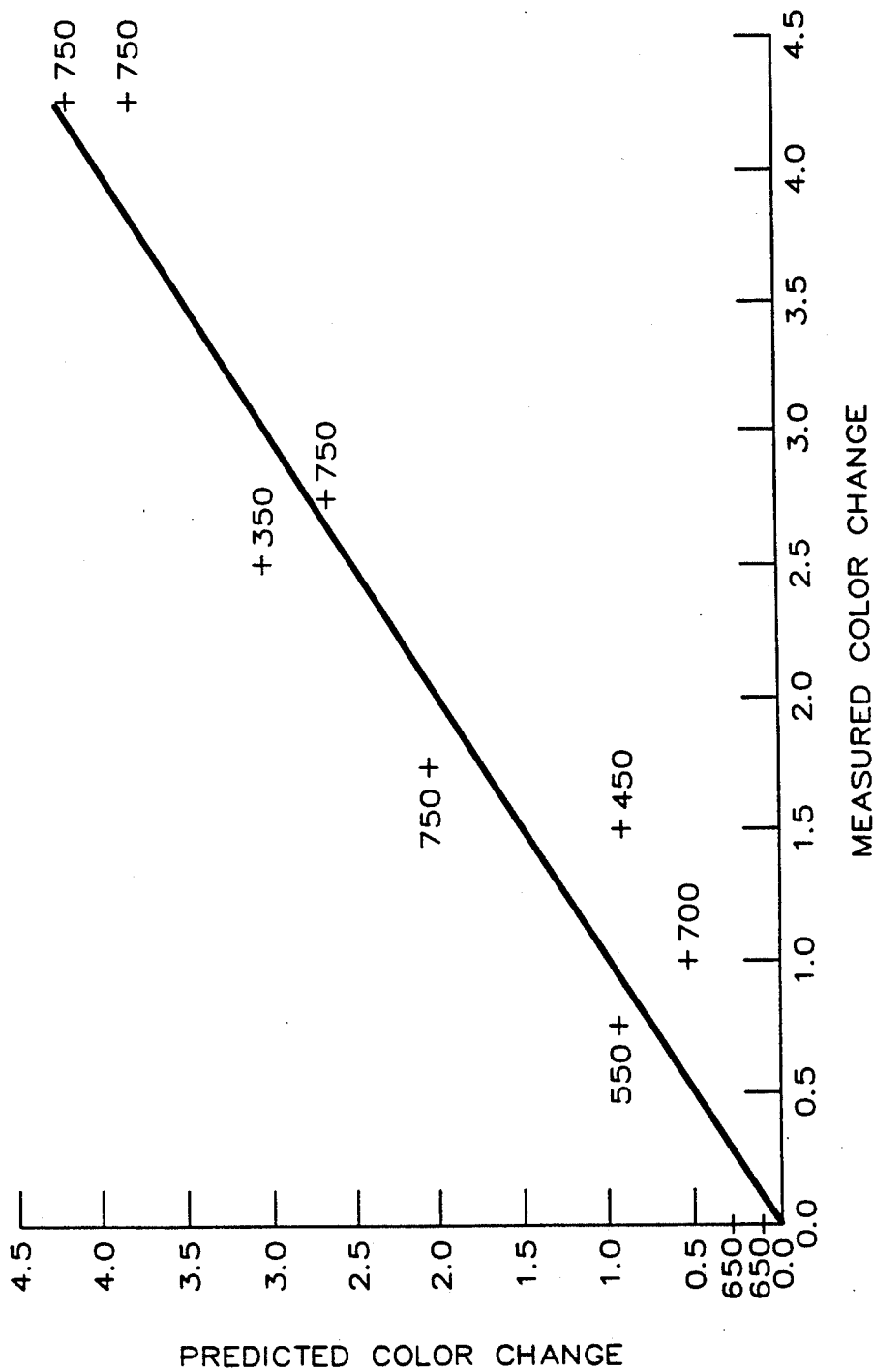
FIG. 2 is a graphical representation of the correlation between the degradation of a hydrotreated light cycle oil and the 375 nm ultraviolet absorption peak of the hydrotreated light cycle oil.

The information in Table II is represented graphically in FIG. 2. From Table II and FIG. 2 it can be seen that the present method of predicting the color change worked for hydrotreated samples.

While this invention has been described with respect to particular embodiments thereof, it is apparent that numerous other forms and modifications of this invention will be obvious to those skilled in the art. The pending claims in this invention generally should be construed to cover all modifications which are within the true spirit and scope of the present invention.

That which is claimed is:

1. A method comprising:
   (a) measuring the absorption of ultraviolet light by a sample of a distillate fuel oil at only one wavelength between about 360 and about 385 nm to obtain a first measurement; and
   (b) determining from said first measurement the amount of degradation of said distillate fuel oil after a period of time.

2. A method according to claim 1 wherein said absorption of ultraviolet light is measured at a wavelength of about 375 nm.

3. A method according to claim 1 wherein step (b) further comprises determining the rate of degradation of said distillate fuel oil.

4. A method according to claim 1 wherein said distillate fuel oil is a hydrotreated distillate fuel oil.

5. A method comprising:
   (a) measuring the absorption of ultraviolet light by a sample of a distillate fuel oil at a wavelength between about 360 and about 385 nm to obtain a first measurement;
   (b) measuring the absorption of ultraviolet light by said sample of distillate fuel oil at a wavelength between about 390 and about 430 nm to obtain a second measurement; and
   (c) determining from a ratio of said first measurement to said second measurement the amount of degradation of said distillate fuel oil after a period of time.

6. A method according to claim 5 wherein step (c) further comprises determining from the ratio of said first measurement to said second measurement the rate of degradation of said distillate fuel oil.

7. A method consisting essentially of:
   (a) measuring the absorption of ultraviolet light through a sample of a distillate fuel oil between 370 and 380 nm to obtain a first measurement;
   (b) measuring the absorption of ultraviolet light through said sample of distillate fuel oil between 390 and 430 nm to obtain a second measurement; and
   (c) determining from said first measurement and said second measurement the amount of degradation of said distillate fuel oil after a period of time.

8. A method according to claim 7 wherein said measurement in step (a) is taken at about 375 nm and said measurement in step (b) is taken at about 395 nm.

9. A method according to claim 8 wherein said measurement in step (a) is taken at 375 nm and said measurement in step (b) is taken at 395 nm.

10. A method according to claim 7 wherein said distillate fuel oil is a hydrotreated distillate fuel oil.

11. A method according to claim 7 wherein said amount of degradation is determined from a ratio of said first measurement to said second measurement.

12. A method consisting of:
    (a) measuring the absorption of ultraviolet light through a sample of a distillate fuel oil at about 375 nm to obtain a first measurement;
    (b) measuring the absorption of ultraviolet light through said sample of distillate fuel oil at about 395 nm to obtain a second measurement; and
    (c) determining from said first measurement and said second measurement the amount of degradation of said distillate fuel oil after a period of time.

13. A method according to claim 12 wherein said distillate fuel oil is a hydrotreated distillate fuel oil.

14. A method according to claim 12 wherein said amount of degradation is determined from a ratio of said first measurement to said second measurement.

* * * * *